United States Patent [19]

Simonian

[11] Patent Number: 4,664,915
[45] Date of Patent: May 12, 1987

[54] COMPRESSED AND FORMED ALKALINE COMPONENT SUITABLE FOR USE IN BUFFERED ASPIRIN PRODUCT

[75] Inventor: Hovsep Simonian, East Orange, N.J.

[73] Assignee: Bristol-Myers Company, New York, N.Y.

[21] Appl. No.: 833,424

[22] Filed: Feb. 21, 1986

Related U.S. Application Data

[63] Continuation of Ser. No. 278,011, Jul. 1, 1981, abandoned.

[51] Int. Cl.⁴ ............... A61K 31/61; A61K 31/605; A61K 33/06; A61K 33/08; A61K 33/10; A61K 33/42; A61L 9/04
[52] U.S. Cl. .................... 424/128; 424/44; 424/154; 424/156; 424/157; 514/163; 514/164
[58] Field of Search ............... 424/44, 154, 156, 157, 424/128; 514/163, 164

[56] References Cited

U.S. PATENT DOCUMENTS

| 3,495,001 | 2/1970 | Leonards | 424/44 |
| 3,518,343 | 6/1970 | Welsh et al. | 424/44 |
| 3,887,700 | 6/1975 | Bouncey et al. | 424/230 |
| 4,339,428 | 7/1982 | Tencza | 424/235 |

OTHER PUBLICATIONS

Burman, Principles of General Chemistry, p. 209 (1969), Allyn & Bacon Inc. Boston.

Primary Examiner—Stanley J. Friedman
Attorney, Agent, or Firm—Gabriel P. Katona

[57] ABSTRACT

A compressed and formed alkaline component suitable for use in a buffered aspirin product. The alkaline component is made of alkaline materials selected from the group consisting of calcium carbonate, magnesium carbonate, magnesium oxide, magnesium hydroxide and mixtures thereof and having incorporated therein citric acid and monobasic sodium phosphate.

21 Claims, No Drawings

COMPRESSED AND FORMED ALKALINE COMPONENT SUITABLE FOR USE IN BUFFERED ASPIRIN PRODUCT

This is a continuing application of application Ser. No. 278,011 dated July 1, 1981, now abandoned.

This invention relates to alkaline components for buffered aspirin products. More particularly, it concerns alkaline components of the above type which are characterized by an improved rate of reaction with acid that is present in the stomach when such products are administered to a subject. The novel combined alkaline component-aspirin products of this invention have utility as analgesics and/or antipyretics that are commonly ascribed to aspirin products. Buffered aspirin products; that is, aspirin products that are formulated so as to simultaneously deliver alkaline material and aspirin to the stomach has been known for a long time. The alkaline materials are administered simultaneously with aspirin, among other reasons, in order to reduce the acidity of the stomach content during this administration and at the same time, react with aspirin to form a soluble salt. In this fashion, it is hoped that the potential of aspirin for gastric irritation and bleeding may be reduced.

The reduction of the acidity in the stomach brought about by the alkaline material is essentially due to the neutralization reaction that takes place between the alkaline material and the acid content of the stomach. Any factor which would increase the rate of this reaction would tend to increase the beneficial effect of the alkaline material when administered with aspirin.

It is customary in the simultaneous administration of alkaline material and aspirin to separate the alkaline material from the aspirin in the unit dosage form. This may take the form of a multi-layered tablet in which the alkaline material is formed into one layer and the aspirin in another layer. In another dosage form, the alkaline layer may be formed into asmall tablet or pellet and the aspirin may be delivered as a powder or granulation. In this case, the small tablet might be loaded into a capsule followed by the powdered or granulated aspirin material. In each of the aforesaid cases, the alkaline material is usually prepared as a granulation and then compressed into a form. In the first case, the form takes the shape as a layer of a multi-layered tablet. In the second case, it takes the form of a discrete tablet or pellet.

It has now been found that the rate of reaction of the alkaline material in the aforesaid compressed forms with the acid content of the stomach can be increased if in shaping said alkaline forms, a combination of citric acid and monobasic sodium phosphate ($NaH_2PO_4$) is incorporated in the alkaline composition. The citric acid and the monobasic sodium phosphate will usually be added in the form as a component of the granulating liquid or solution. Moreover, best results are obtained with alkaline materials selected from the group consisting of magnesium carbonate, calcium carbonate, magnesium oxide, magnesium hydroxide and combinations thereof. Of special interest are the following combinations of alkaline materials (1) MgO and $CaCO_3$; (2) $Mg(OH)_2$ and $CaCO_3$; (3) MgO, $MgCO_3$ and $CaCO_3$; (4) $Mg(OH)_2$, $MgCO_3$ and $CaCO_3$; (5) $MgCO_3$ and $CaCO_3$; and (6) MgO and $Mg(OH)_2$.

It is accordingly an object of the present invention to provide a compressed an shaped alkaline component for a buffered aspirin product which increases the rate of reaction of said alkaline component with the acid content of the stomach.

It is also an object of this invention to provide a process for alleviating pain and/or fever in a subject by administering to said subject the product of the foregoing object.

Other and more detailed objects of this invention will be apparent from the following description and claims.

Although the formed compressed alkaline component of the present invention may be used in conjunction with aspirin in a variety of modes (e.g. as multi-layered tablets) for convenience of description, emphasis for the most part will be placed on those dosage forms in which the alkaline component is formed into at least one discrete tablet or pellet which is then loaded into a capsule along with a powdered or granulated aspirin mix. Such a system is described in the U.S. patent application to Thomas M. Tencza, Ser. No. 179,191 filed Aug. 18, 1980.

This mode of the present invention provides capsules containing analgesic compositions in which the active analgesic ingredient is normally unstable. Aspirin may be the sole active analgesic ingredient. However, other active analgesics in addition to aspirin, as well as, other pharmaceutically active ingredients with or without non-aspirin analgesics may be contained in the capsule.

The small alkaline tablet which forms part of the analgesic product of this mode of the present invention will contain a combination of the alkaline materials mentioned above. In addition, it may also contain other ingredients which are compatible with the alkaline material in the tablet.

As used herein, the term "aspirin mixture" refers to that powder and/or granular portion of the composition that contains the aspirin but may also contain other compatible powder or granular materials. The term "alkaline tablet" refers to the small tablet which contains the alkaline material but may also contain other compatible ingredients.

The term "magnesium oxy component" as used in the present specification means a material selected from the group consisting of magnesium oxide, magnesium hydroxide or a combination of magnesium oxide and magnesium hydroxide.

Unless otherwise specified, percent is given as percent by weight based on the total weight of the product contained in the dosage form.

ALKALINE TABLET

The alkaline tablet used in this mode of the invention is a small tablet dimensioned so that it can be conveniently dropped into the open end of a capsule which is of a suitable size for use in this invention e.g. #0, #1 and #2. The capsules can be either hard shell or soft shell gelatin capsules, with hard shell preferred. The alkaline tablets will usually comprise the combination of alkaline materials described above that are formed into a granulation by a wet granulation process to provide a material that is readily compressible to form a tablet.

The wet granulation process will usually involve preparing a granulating liquid comprising an aqueous vehicle having dissolved therein citric acid and monobasic sodium phosphate. The quantity of these ingredients contained in the granulating liquid may vary somewhat; usually, however, they will fall within the following percent ranges based on the total weight of the granulating liquid: citric acid from about 1% to about 5%; monobasic sodium phosphate from about 1% to about 5%. Other ingredients commonly contained in a granulating liquid may also be contained in the granulating liquid employed in this invention.

In preparing the alkaline granulation, the granulating liquid containing the citric acid and monobasic sodium phosphate is mixed with the alkaline mix described in more detail below. This is then passed through a screen having suitable size openings to form granules which are then dried. The granules so formed are then passed through an oscillating screen of suitable size to provide granules that can be compressed into an alkaline tablet.

The quantity of citric acid and monobasic soidum phosphate that will be contained in the alkaline tablet or other similar formed and compressed alkaline component will vary somewhat. Usually, this will be within the following ranges based on the total weight of said alkaline component: citric acid from about 1% to about 5%; monobasic sodium phosphate from about 1% to about 5%.

The total quantity of alkaline material as a combination of the alkaline ingredients mentioned above may vary somewhat as long as they can be formed into a suitable alkaline sized tablet. The total amount of alkaline material is usually related to the amount of aspirin contained in the aspirin component. Typically, the amount of alkaline material is present in the tablet at a level of from about 20% to about 150% by weight based on the weight of aspirin contained in each capsule. The quantity employed will depend on the acid consuming capacity (ACC value) of the alkaline material.

To get the full benefit of the alkaline component insofar as it has an effect on the absorption rate of the aspirin, it is important that the alkaline tablet have a fast disintegration rate. Good disintegration rates are obtained where the alkaline material consists of a combination of magnesium carbonate, calcium carbonate and the magnesium oxy component as defined above.

The quantity of alkaline material contained in the compressed alkaline component of this invention may vary somewhat. As used herein, the term alkaline component refers to the formed and compressed alkaline section of the dosage forms. This includes the separate alkaline tablet or tablets that are to be included in a capsule along with aspirin or it may be a layer of a multi-layered tablet. The formed and compressed alkaline component ordinarily will contain other ingredients besides alkaline materials.

Usually, the quantity of alkaline material that will be contained within the alkaline component will comprise between about 35% to about 95% by weight based on the total weight of the compressed and formed alkaline component. Most often, however, alkaline material will constitute between about 75% to about 95% on the same weight basis.

The relative amounts of calcium carbonate, magnesium carbonate and magnesium oxy component that will be contained in the compressed and formed alkaline component may also vary. This will largely be determined by the acid consuming capacity requirement for the particular dosage form. Generally, calcium carbonate, when present, will comprise up to 95% by weight of the compressed and formed alkaline component but most often this will not exceed 75% on the same weight basis. Similarly, when magnesium carbonate is utilized, this will ordinarily not exceed 95% by weight of said alkaline component. Again, usually this will not exceed 35% on the same weight basis.

The magnesium oxy component in the form of magnesium oxide, magnesium hydroxide or combinations of magnesium oxide and magnesium as indicated above may constitute the sole alkaline material obtained in the alkaline component or may be employed in conjunction with the other alkaline materials. When it constitutes all or a part of said alkaline component, it may be used at a level up to and including about 95% by weight based on the weight of said alkaline component. However, this will ordinarily not exceed about 75% by weight on the same weight basis.

In the preferred form of this invention, all three types of alkaline materials i.e. calcium carbonate, magnesium carbonate and magnesium oxy component are used simultaneously. In this case, the percent ranges for the respective alkaline materials based on the total weight of the compressed and formed alkaline component are as follows:

calcium: carbonate: from about 20% to about 75%
magnesium carbonate: from about 5: to about 35%
magnesium oxy component: from about 10% to about 75%

The magnesium oxy component may be added to the pregranulation alkaline mix as magnesium oxide, magnesium hydroxide or as a combination of magnesium oxide and magnesium hydroxide. Since the granulation step involves wetting the pre-granulation mix with an aqueous granulating liquid when magnesium oxide is used, some part or all of the magnesium oxide may be converted into magnesium hydroxide.

It is also advantgeous to incorporate a disintegrant in the alkaline tablet of the present product to increase the rate at which it disintegrates in the stomach. A variety of materials are known in the tabletting art which will accomplish this function. These include such materials as corn starch, potato starch, wheat starch, modified starch (e.g. Sta-Rex) and sodium carboxymethyl starch (e.g. Primojel). Ordinarily, such materials are present in the alkaline tablet at a level in the range of from about 5% to about 25% by weight based on the total weight of the alkaline tablet.

Other ingredients may be added to the alkaline tablet to improve its physical or organoleptic characteristics or to facilitate the manufacture of the alkaline tablet. A lubricant such as magnesium stearate, stearic acid or silicone fluid may be added to facilitate the tabletting of the alkaline granulation.

The alkaline tablet is dimensioned so that it will contain a maximum amount of weight of material in a minimum volume so it can be readily dropped into a gelatin capsule e.g. #0 geltin capsule. This is accomplished by forming the alkaline tablet as a spheroid or near-spheroid having a diagonal dimension of no greater than the diameter of the open end of the capsule. Usually, the diameter of the tablet at its greatest dimension will be in the range of from about 0.225" to about 0.255" for #0 gelatin capsule. For different sized capsules, the appropriate diameter tablet will be used.

Because of the difficulty in compressing a granulation into a true spheroidal tablet in the preferred practice of this invention, a modified deep ball punch is employed. This gives a modified spheroidal tablet having the form of a solid cylinder provided with an upper and lower dome. In this case, the important dimension is the diameter of the tablet in longitudinal cross section that extends from the top of one vertical side to the bottom of the other vertical. A suitable diameter is in the range of from about 0.210" to about 0.255" for #0 gelatin capsule. The punch size will be changed for different gelatin capsule size so that the weight of the tablet and the diameter of the tablet will be reduced proportionally to satisfy the ACC meq. alkalinity to the q.s. aspirin used.

ASPIRIN MIXTURE

The principal ingredient on a weight basis in the aspirin mixture will usually be aspirin. This will ordinarily take the form of a powder or dry granulation that may vary widely in particle size. In the typical cases, this will usually fall within the range of from about 100% which pass through a 12 mesh screen to about 100% which pass through a 80 mesh screen. "Micronized" aspirin well known to those skilled in this art may also be used.

The lower limit of aspirin which will be contained in the capsule of this invention will be about 81 mg. for pediatric use. For adults, this will usually be about 325 mg. The upper limit is limited only by the feasibility of swallowing the size of the capsule that is required to contain this material. As a practical matter, this will rarely exceed about 650 mg. of aspirin per capsule. For the usual adult use, between 325 mg. to 500 mg of aspirin will be contained in each capsule. In the preferred embodiment, the aspirin level will be about 500 mg/capsule. The ordinary single dose will be one or two capsules for adults.

The aspirin mixture may also contain conventional excipients which are compatible with aspirin and which are well known to those skilled in the pharmaceutical arts such as, for example, starch, modified starch (e.g. product sold under the trade name "Sta-Rx"), microcrystalline cellulose (Avicel or Elcema), sodium carboxymethyl starch (Explotab, Primojel).

The quantity of excipient in each capsule can vary depending upon the quantity of aspirin contained therein and the size of the capsule. Typically, the quantity of excipient in each capsule is within the range of from about 0% to about 50% by weight based on the weight of the aspirin contained in the mixture.

The aspirin mixture may also contain a lubricant which serves to facilitate the flow of powder or granular materials during filling and processing. There are a number of lubricants well known to those skilled in this art that may be employed. For example, mention may be made of the Silicone Fluids (i.e. polydimethylsiloxane), fumed silicone dioxide (e.g. Cab-O-Sil M-5 or Aeosil 200), light mineral oil, and polyethylene glycol (Carbowax 400), etc.

The quantity of lubricant in the aspirin mixture is related to the quantity of aspirin present. Typically, the quantity of lubricant in each capsule is within the range of from about 0.1% to about 5% by weight based on the weight of the aspirin contained in the mixture.

In addition to aspirin, other pharmaceutically active ingredients may be contained in the aspirin mixture. These may be other analgesics, analgesic potentiators, antihistamines, decongestants, and antitussive agents. By way of illustration of such other pharmaceutically active ingredients, mention may be made of acetaminophen, caffeine, chlorpheniramine maleate, phenylpropanolamine HCl, dextromethorphan, codeine, doxylamine succinate, phenindamine tartrate and other salts thereof and surfactants such as sodium lauryl sulfate, polyvinylpyrrolidone, polyoxyethylene(20)sorbitan monooleate (Tween 80), etc.

After the alkaline tablets are formed, they are fed to a filling station where each is inserted into the body of a capsule and the capsule containing the alkaline tablet is passed on to a second station where it receives the powdered aspirin mixture. After receiving the powdered aspirin mixture, the capsule is capped with the upper half of the capsule and the product is completed.

The capsules that are employed in the present invention may be conventional gelatin capsules that are well known to those skilled in this art. These may vary somewhat in size but usually they will be #0, #1, #2 and #3. Since a fast rate of absorption of aspirin into the bloodstream is a desirable feature, it is advantageous to employ a capsule which in itself is fast dissolving. With this in mind, it is useful to include in the gelatin material that constitutes the capsule about 10% by weight of calcium carbonate based on the total weight of the capsule mentioned.

As indicated above, the formed alkaline component of this invention may form part of a multi-layered tablet also containing aspirin. A typical case of this character is a two-layered tablet in which the alkaline granulation described above in preparing the "alkaline tablet" may be used in forming one layer of the tablet and the "aspirin mixture" also described above is used to form the aspirin layer of such a two-layered tablet. The technique for making the two-layered tablets is well known to those skilled in this art. In general, this involves feeding a measured quantity of the aspirin granulation into a tablet punch, optionally tamping the aspirin granulation down to form a first layer, feeding a measured quantity of the alkaline granulation into said tablet punch to cover said aspirin layer and to form a second layer and then compressing the layers together.

The following Examples are given to further illustrate the present invention. It is to be understood, however, that the invention is not limited thereto.

EXAMPLE 1

Formula RF #2034 (Capsule)

| Dosage Unit Amount mg/tablet | Item No. | Ingredients | Gms/10,000 Tablets |
|---|---|---|---|
| PART I: (A) Alkaline Granulation | | | |
| 38.24 | 1 | Magnesium oxide U.S.P. heavy | 382.4 |
| 23.90 | 2 | Magnesium carbonate U.S.P. | 239.0 |
| 95.60 | 3 | Calcium carbonate U.S.P. heavy** | 956.0 |
| 2.39 | 4 | Citric Acid, anhy. powder | 23.9 |
| 2.39 | 5 | Monosodium phosphate, anhy. (NaH$_2$PO$_4$) | 23.9 |
| q.s. to dissolve 4 & 5 | 6 | Water, deionized | q.s. to dissolve 4 & 5 |
| 2.87 | 7 | Starch, corn | 28.7 |
| q.s. to suspend 7 | 8 | Water, deionized | q.s. to suspend 7 |
| 16.25 | 9 | Starch, corn | 162.5 |
| 181.64 | | | 1816.4 |
| | | (B) Alkaline Tablet | |
| 181.64 | 10 | Alkaline Granulation | 1816.4 |
| Range 0.36-0.72++ | (A) 11 | Magnesium stearate, U.S.P. | 3.6 |
| 182.00 | | | 1820.0 |

Procedure:
(A) Alkaline Granulation
a. In ribbon blender charge 1, 2 and 3. Mix for 5 minutes.

b. Dissolve 4 and 5 in 6 at 100° C.
c. Suspend 7 in 8 and add to (b) while agitating (1 minute).
d. Add hydrolyzed starch (b,c) to (a) and mix for 3-5 minutes.
e. Add 9 to (a) mix another 1-2 minutes.
f. Pass (e) through Tornado Mill with a ¾″ screen.
g. Dry in Fluid Bed Dryer (inlet temp. 8°-90° C.) outlet temp. 35°-36° C.) to a moisture of 1-2% maximum.
h. Pass (g) through oscillator with a 10 mesh screen.

(B) Alkaline Tablet
a. In a V-blender mix 10 & 11 for 15 minutes.
b. Compress to the specifications below:
Appearance: White spherical tablet
Taste, odor: Alkaline taste
Moisture: Part A—1-2% max.
ACC meq. 4.3 per tablet
Punch: 7/32″ special spherical punch
Weight: 182 mg.
Thickness++: 0.210″-0.230″ (cup depth 0.050″-0.057″)
Disintegration: USP Basket App., Water 37° C.—10-30 sec.
Diagonal Measurement 0.260″
Tablet Wt.: 182 mg±5%

| Dosage Unit Amount mg/capsule | Item No. | Ingredients | Prepared for 200,000 capsules Gms/4,440 |
|---|---|---|---|
| PART II: (A) Excipient and Lubricant | | | |
| 21.20 Range 10-30 | 1 | Modified starch 1500 Sta-Rx 1500 | 4,000 (Before drying 4,240) |
| 2.00 Range 2-5 | 2 | Dimethylpolysiloxane Fluid 360 Medical Type/350 centistokes | 400 |
| 0.20 | 3 | Polyoxyethylene(20) sorbitan monooleate (Tween 80) | 40 |
| 23.40 | | | 4,440 |
| | | (B) Aspirin Mixture | |
| 500.00 | 4 | Aspirin 80 mesh | 100,000 |
| 22.20 | 5 | Excipient & lubricant | 4,440 |
| 522.20 | (A) | | 104.440 |

Procedure
(A) Excipient and Lubricant
a. Place 1 in a mixer and add 2 and 3 (previously mixed). Mix for 5 minutes.
b. Dry (a) in a Fluid Bed Dryer (inlet temp. 80° C.—outlet temp. 55°-60° C.) approx. 15 minutes.

(B) Aspirin Mixture
a. In a Ribbon blender, charge 4 and 5. Mix for 15 minutes.
b. Pass (a) through oscillator with an 8 mesh screen.
or (1)
(a) Dry Sta-Rx in oven at 40°-50° C. to 4% maximum moisture.
b. In Ribbon blender, mix Sta-Rx and aspirin for 5 minutes. Then add premixed silicone fluid and Tween 80, mix another 5 min. Pass through #8 mesh screen.

(2)
a. Buy dry Sta-Rx 4% maximum moisture.
b. Same as (1 b)

Appearance: White oily powder
Taste, Odor: Slight Tween odor
Moisture (A) Excipient & Lubricant 4% max. (Range 1-4%)

Capsule Filling Procedure

Alkaline tablets prepared in accordance with the procedure described above in Part I (A) and (B) are inserted into capsules (capsule size #0) with an automatic filler. The aspirin mixture prepared in accordance with the procedure described above in Part II (A) and (B) is fed to a hopper and is used to load the capsule in accordance with the following specifications:

| Ingredients | mg/capsule |
|---|---|
| Aspirin | 500.00 |
| Excipient | 22.20 ± 5% |
| Alkaline Tablet | 182.00 |
| Empty caps. | 100.00 |
| | 804.20 |

Range: 764 mg-844 mg.

EXAMPLE 2

Formula 1565-73 (Capsule)

| Alkaline Tablet Ingredients | mg/tablet | gms/batch |
|---|---|---|
| Magnesium oxide | 40 | 1600 |
| Magnesium carbonate | 25 | 1000 |
| Calcium carbonate | 100 | 4000 |
| Starch | 20 | 800 |
| Citric Acid | 2.5 | 100 |
| $NaH_2PO_4$ | 2.5 | 100 |
| | 190.0 | 7600 |
| Moisture less than | 1% | |
| Add Magnesium stearate | 0.38 | |
| | 190.38 | |

Disintegration: 10-20 seconds
Thickness: .215″-.220″
ACC value = 4.5 meq.

| Aspirin Mix Ingredients | mg/tablet |
|---|---|
| Aspirin (80 mesh) | 450. |
| Aspirin (micronized) | 50. |
| Sta-Rx (starch) | 20. |
| Silicone fluid | 2. |
| Tween 80 | .30 |
| | 522.30 |

Using automatic or semi-automatic filling equipment #0 gelatin capsules were filled with one alkaline tablet each and the specified amount of aspirin mix. Each capsule had the following specifications:

| Alkaline tablet | 190.38 mg. |
|---|---|
| Aspirin mix | 522.30 mg |
| Total composition | 712.68 mq ± 3% |
| Empty caps. | 100.00 mg. |
| Total Product Weight | 812.68 mg. |

EXAMPLE 3

Formula 1565-82 (Capsule)

| Alkaline Tablet Ingredients | mg/tablet |
|---|---|

-continued

| | | |
|---|---|---|
| Magnesium hydroxide | 65 | |
| Magnesium carbonate | 25 | |
| Calcium carbonate | 78 | Sturcal H |
| Citric acid | 2.5 | |
| NaH$_2$PO$_4$ | 2.5 | |
| Starch | 3 | |
| Starch | 17 | |
| | 173 | |
| Moisture: 1.5% | | |
| Alkaline granulation: | 193 | |
| Magnesium stearate: | 0.386 | |
| | 193.386 | |
| Weight: 0.193.38 | | |
| Thickness: 0.235" | | |
| Diagonal: 0.250" ± .005 | | |
| Disintegration time: 10–30 sec. | | |

Alkaline tablets made in accordance with the above formula and specifications may be loaded into #0 gelatin capsule, one tablet for each capsule. The aspirin mix described in Example 2 may then be loaded into each capsule in the measured quantity also specified in Example 2 and then the capsule is capped.

EXAMPLE 4

Formula CL 1565-85 (Capsule)

| Ingredients | mg/capsule |
|---|---|
| (A) Aspirin Mix | |
| Aspirin 80 crystals | 325. |
| Sta-Rx (dry) | 14. |
| Silicone Fluid 360 | 1.4 |
| Tween 80 | 0.15 |
| | 340.55 |
| (B) Alkaline Tablet | |
| Same as alkaline tablet of Example 1. | |

Two alkaline tablets, as described in Example 1, each weighing about 183 mg were prepared from the alkaline mix and placed in an empty #0 gelatin capsule. The aspirin mix is then added to specifications and the cap of the capsule is applied.

EXAMPLE 5

Formula CL 1565-84A (Two-layered Tablet)

| Ingredients | mg/tablet |
|---|---|
| (A) Aspirin Layer | |
| Aspirin 12/50 (granulation containing 10% Starch) | 362. |
| (B) Alkaline Layer | |
| Alkaline mixture of Example 1 before compression into tablet (Formula RF #2034) | 300. |
| | 662. |

This tablet had a thickness of within 0.205–0.210 and an ACC value of 7.0 meq.

EXAMPLE 6

Formula CL 1565-84B (Two-layered Tablet)

| Ingredients | mg/tablet |
|---|---|
| (A) Aspirin Layer | |
| Aspirin 12/50 | 362. |
| (granulation containing 10% Starch) | |
| (B) Alkaline Layer | |
| Alkaline mixture of Example 1 before compression into tablet (Formula RF #2034) | 360. |
| | 722. |

This tablet had a thickness of from 0.45"–0.220" and an ACC value of 8.5 meq.

EXAMPLE 7

Formula CL 1565-84C (Two-layered tablet)

The same as Example 6, except that tablet had a thickness of 0.230".

EXAMPLE 8

Formula CL 1565-84D (Two-layered tablet)

The same as Example 6, except that tablet had a thickness of 0.235"–0.240".

EXAMPLE 9

Formula CL 1565-84E (Two-layered tablet)

The same as Example 6, except that tablet had a thickness of 0.245".

EXAMPLE 10

Formula CD 1854-23 (Two-layered tablet capsule shape)

| Ingredients | mg/tablet |
|---|---|
| LAYER I | |
| Aspirin 12/50 (granulation containing 10% starch) | 555.5 |
| LAYER II | |
| Magnesium oxide | 63.87 |
| Magnesium carbonate | 39.92 |
| Calcium carbonate | 159.68 |
| Citric acid | 3.99 |
| Monosodium phosphate | 3.99 |
| Corn Starch, Part I | 4.79 |
| Corn Starch, Part II | 27.15 |
| Magnesium stearate | 0.61 |
| | 304.00 |
| | 859.5 |

ACC value: 7.18 meq.

Compressed on Stokes Rotary press equipped with capsule shaped punches.

EXAMPLE 11

Formula 1595-183 (Two-layered tablet)

| Ingredients | mg/tablet |
|---|---|
| LAYER I | |
| Aspirin starch granulation 12/50 (Aspirin 7½ gr) | 541.7 |
| LAYER II | |
| Magnesium oxide | 88.96 |
| Magnesium carbonate | 55.60 |
| Calcium carbonate | 222.40 |
| Citric acid | 5.56 |
| Monosodium phosphate | 5.56 |
| Corn Starch, Part I | 6.67 |
| Corn Starch, Part II | 37.81 |

-continued

| Ingredients | mg/tablet |
|---|---|
| Magnesium stearate | 0.84 |
| | 423.4 |
| | 965.1 |

ACC value: 10 meq.

EXAMPLE 12

Formula 1595-182 (Two-layered tablet)

| Ingredients | mg/tablet |
|---|---|
| LAYER I | |
| Aspirin starch granulation 12/50 (Aspirin 7½ gr) | 541.7 |
| LAYER II | |
| Magnesium oxide | 63.87 |
| Magnesium carbonate | 39.92 |
| Calcium carbonate | 159.68 |
| Citric acid | 3.99 |
| Monosodium phosphate | 3.99 |
| Corn Starch, Part I | 4.79 |
| Corn Starch, Part II | 27.15 |
| Magnesium stearate | 0.61 |
| | 304.00 |
| | 845.7 |

ACC value: 7.2 meq.

To compare the relative speed of reaction of the formed alkaline component of the present invention containing the citric acid and monobasic sodium phosphate with one in which these components are absent, the following in vitro experiments were carried out. Alkaline tablets having the formulas set out below were prepared:

Formula CL 1565-83A

| Alkaline Tablet: | |
|---|---|
| Ingredients | mg/tablet |
| Magnesium carbonate | 23.90 |
| Calcium carbonate (Sturcal H) | 95.60 |
| Magnesium oxide | 38.24 |
| Starch | 19.12 |
| | 176.86 |
| Magnesium stearate | 0.35 |
| | 177.21 |

Formula CL 1565-83B

The same as 1565-83A, except that the $CaCO_3$ was sourced from Pfizer.

Formula CL 1565-73

See Example 2, Alkaline tablet.

Formula CL 1565-82

See Example 3, Alkaline tablet.

The acid consuming capacity (ACC value) for each of the aforesaid alkaline tablets were as follows:

| CL 1565-82 | 4.1 meq |
|---|---|
| CL 1565-73 | 4.3 meq |
| CL 1565-83A | 3.75 meq |
| CL 1565-83B | 4.1 meq |

Procedure:

A Radiometer pH stat, Model 79752 was used for this work. The alkaline material is added to the sample cup along with 40 ml of 0.01N HCl. The apparatus is set to maintain the pH at 2. The instrument will automatically add acid (0.2N) to keep the pH constant at 2. As the antacid reacts it will attempt to raise the solution pH. A strip chart recorder plots the addition of acid versus time. An antacid which reacts rapidly will cause the acid to be added rapidly, resulting in a steep slope for the recorder plot.

Tests:

To determine the rate of reaction of the respective alkaline tablets with acid, two measurements were made. The first measurement was the initial slope of the curve that is generated by plotting the volume of test acid added to the reaction beaker over time to maintain the constant pH (pH 2). The other measurement is the time in minutes that it takes to consume 50% of the acid consuming capacity of the test alkaline tablet. Five runs were made with each of the test alkaline tablets. The results of these runs are reported in Table I below:

TABLE I

| CL 1565-73 190 mg w/citro-phosphate | | CL 1565-82 193 mg w/citro-phosphate | | CL 1565-83A 177 mg without citrophosphate | | CL 1565-83 without citric acid | |
|---|---|---|---|---|---|---|---|
| slope | T min 50% meq | slope | T min 50% meq | slope | T min 50% meq | slope | T min 50% meq |
| 21.4 | 0.6 | 23.3 | 0.5 | 10.1 | 1.9 | 9.1 | 2.0 |
| 20.5 | 0.6 | 24.7 | 0.6 | 11.1 | 1.7 | 8.8 | 2.0 |
| 22.1 | 0.5 | 20.3 | 0.6 | 7.9 | 2.1 | 9.7 | 2.1 |
| 22.8 | 0.6 | 23.1 | 0.6 | 10.2 | 1.8 | 8.1 | 2.0 |
| 20.0 | 0.6 | 21.7 | 0.6 | 9.2 | 2.0 | 8.0 | 2.1 |
| M = 21.4 | 0.6 ± 0 | 22.6 ± 1.7 | 0.6 ± 0 | 9.7 ± 1.2 | 1.9 ± 1.2 | 8.7 ± 0.7 | 2.0 ± 0.1 |
| | | CR = 0.9 | | CR = 2.2 | | CR = 2.5 | |

The "CR" value reported in Table I is the comparison ratio and is obtained from the following formula:

$$CR - \text{comparison ratio} = \frac{\text{Slope } (M) \text{ standard}}{\text{Slope } (M) \text{ sample}}$$

where the mean slope value (M) for CL 1565-73 is taken as the standard. This is introduced to minimize the variation in results that may be due to variations in stirring.

An examination of this Table will show that by all the criteria, the reaction rate of the alkaline tablets containing the citric acid and monobasic sodium phosphate i.e. Formulas CL 1565-73 and CL 1565-82 was greater when compared with those alkaline compositons that did not contain these materials.

What is claimed is:

1. A compressed and formed alkaline component adapted for use in conjunction with an aspirin containing composition so as to provide a buffered aspirin product; said compressed alkaline component comprising an effective buffering amount of an alkaline material which is the predominant part of said alkaline component, is selected from the group consisting of calcium carbonate, magnesium carbonate, a magnesium oxy component and mixtures; said magnesium oxy component being selected from the group consisting of magnesium oxide, magnesium hydroxide and a combination of magnesium oxide and magnesium hydroxide; said compressed alkaline component also having incorporated therein as minor components citric acid and monobasic sodium phosphate to enhance the acid neutralizing reaction rate of said alkaline component.

2. A compressed and formed alkaline component according to claim 1 in which said predominant part is in the range of from about 35% to about 95% by weight based on the total weight of said alkaline component and said minor components each comprise from about 1% to about 5% by weight.

3. A compressed and formed alkaline component according to claim 2 in which the alkaline material in said component is in the range of from about 75% to about 95% by weight based on the total weight of said alkaline component.

4. A compressed and formed alkaline component according to claim 1 containing at least one of said alkaline materials and in which the various ingredients are present in said compressed alkaline component within the following ranges based on the total weight of said compressed alkaline component:
 calcium carbonate: from about 0% to about 95%
 magnesium carbonate: from about 0% to about 95%
 magnesium oxy component: from about 0% to about 95%
 citric acid: from about 1% to about 5%
 monobasic sodium phosphate: from about 1% to about 5%.

5. A compressed and formed alkaline component according to claim 1 containing at least two of said alkaline materials and in which the various ingredients are present in said compressed alkaline component within the following ranges based on the total weight of said compressed alkaline component:
 calcium carbonate: from about 0% to about 75%
 magnesium carbonate: from about 0% to about 35%
 magnesium oxy component: from about 0% to about 75%
 citric acid: from about 1% to about 5%
 monobasic sodium phosphate: from about 1% to about 5%.

6. A compressed and formed alkaline component according to claim 1 containing at least three of said alkaline materials in which the various ingredients are present in said compressed alkaline component within the following ranges based on the total weight of said compressed alkaline component:
 calcium carbonate: from about 20% to about 75%
 magnesium carbonate: from about 5% to about 35%
 magnesium oxy component: from about 10% to about 75%
 citric acid: from about 1% to about 5%
 monobasic sodium phosphate: from about 1% to about 5%.

7. A unit dosage form comprising a compressed and formed alkaline component and an aspirin containing composition; said compressed alkaline component comprising as a predominant part an effective buffering amount of an alkaline material selected from the group consisting of calcium carbonate, magnesium carbonate, a magnesium oxy component and mixtures thereof; said magnesium oxy component being selected from the group consisting of magnesium oxide, magnesium hydroxide and a combination of magnesium oxide and magnesium hydroxide; said compressed alkaline component also having incorporated therein as minor components citric acid and monobasic sodium phosphate to enhance the acid neutralizing reaction rate of said alkaline component; said aspirin being present in said dosage form in therapeutically effective amounts.

8. A unit dosage form according to claim 7 in the form of a capsule containing the compressed alkaline component in the form of at least one tablet or pellet and the aspirin in the form of a powder or granulation.

9. A unit dosage form according to claim 7 in the form of a multi-layered tablet, said compressed alkaline component comprising one layer of said tablet and said aspirin being contained in another layer of said tablet.

10. A unit dosage form according to claims 7, 8 or 9 in which said predominant part is present in said dosage form at a level of from about 20% to about 150% by weight based on the weight of the aspirin in said unit dosage form.

11. A unit dosage form according to claims 7, 8, 9, or 10 in which the compressed alkaline component contains at least one of said alkaline materials and in which the various ingredients are present in said compressed alkaline component within the following ranges based on the total weight of said compressed alkaline component:
 calcium carbonate: from about 0% to about 95%
 magnesium carbonate: from about 0% to about 95%
 magnesium oxy component: from about 0% to about 95%
 citric acid: from about 1% to about 5%
 monobasic sodium phosphate: from about 1% to about 5%.

12. A unit dosage form according to claims 7, 8, 9 or 10 in which the compressed alkaline component contains at least two of said alkaline materials and in which the various ingredients are present in said compressed alkaline component within the following ranges based on the total weight of said compressed alkaline component:
 calcium carbonate: from about 0% to about 75%
 magnesium carbonate: from about 0% to about 35%
 magnesium oxy component: from about 0% to about 75%
 citric acid: from about 1% to about 5%
 monobasic sodium phosphate: from about 1% to about 5%.

13. A unit dosage form according to claims 7, 8, 9 or 10 in which the compressed alkaline component contains at least three of said alkaline materials and in which the various ingredients are present in said compressed alkaline component within the following ranges based on the total weight of said compressed alkaline component:
 calcium carbonate: from about 20% to about 75%
 magnesium carbonate: from about 5% to about 35%
 magnesium oxy component: from about 10% to about 75%
 citric acid: from about 1% to about 5%
 monobasic sodium phosphate: from about 1% to about 5%.

14. A unit dosage form comprising a capsule containing an alkaline component in the form of one or more tablets and an aspirin mixture in powder or granular form; said alkaline component comprising a mixture containing calcium carbonate, magnesium carbonate and a magnesium oxy component selected from the group consisting of magnesium oxide, magnesium hydroxide and a mixture of magnesium oxide and magnesium hydroxide and also having incorporated therein as minor components citric acid and monobasic sodium phosphate; said alkaline component being present in said capsule at a level of from about 150 mg to about 400 mg per capsule and the aspirin being present in said capsule at a level of from about 81 mg to about 650 mg, the relative proportions of the ingredients in said alkaline component based on the total weight of said alkaline component being as follows:

calcium carbonate: from about 20% to about 75%
magnesium carbonate: from about 5% to about 35%
magnesium oxy component: from about 10% to about 75%
citric acid: from about 1% to about 5%
monobasic sodium phosphate: from about 1% to about 5%.

15. A unit dosage form according to claim 14 in which the aspirin is present in said capsule at a level from about 325 to about 650 mg. per capsule.

16. A unit dosage form comprising a multi-layered tablet containing an alkaline layer and an aspirin layer; said alkaline layer comprising a mixture containing calcium carbonate, magnesium carbonate and a magnesium oxy component selected from the group consisting of magnesium oxide, magnesium hydroxide and a mixture of magnesium oxide and magnesium hydroxide and also having incorporated therein as minor components citric acid and monobasic sodium phosphate, said alkaline material being present in said alkaline layer at a level of from about 150 mg to about 400 mg per unit dosage form and the aspirin being present in said tablet at a level of from about 81 mg to about 650 mg per unit dosage form, the relative portions of the ingredients in said alkaline layer based on the total weight of said alkaline layer being as follows:

calcium carbonate: from about 20% to about 75%
magnesium carbonate: from about 5% to about 35%
magnesium oxy component: from about 10% to about 75%
citric acid: from about 1% to about 5%
monobasic sodium phosphate: from about 1% to about 5%.

17. A unit dosage form according to claim 16 in which the aspirin is present in said unit dosage form at a level of from about 325 mg to about 650 mg per unit dosage form.

18. A process for forming a compressed alkaline component which comprises forming as a predominant part a dry mix comprising calcium carbonate, magnesium carbonate and a magnesium oxy component selected from the group consisting of magnesium oxide, magnesium hydroxide and a combination of magnesium oxide and magnesium hydroxide, wetting said mixture with a granulating liquid containing as minor ingredients citric acid and monobasic sodium phosphate, granulating said wetted mixture and then compressing said granulated material to form a compressed alkaline component.

19. A process according to claim 18 in which said citric acid is present in said granulating liquid at a level in the range of from about 1% to about 5% by weight based on the total weight of the granulating liquid and said monobasic sodium phosphate is present in said granulating liquid at a level in the range of from about 1% to about 5% by weight based on the total weight of granulating liquid.

20. A process for alleviating pain and/or reducing the fever in a subject which comprises administering to said subject a therapeutically effective number of unit dosage forms defined in 7, 8, 9, 10, 11, 12, 13, 14, 15, 16 or 17.

21. A composition comprising an effective alkalizing amount of an alkaline material which is the predominant part of that composition, said alkaline material being one or more of calcium carbonate, magnesium oxide, magnesium hydroxide, and a minor concentration of citric acid and monosodium phosphate to enhance the acid neutralizing rate of the alkaline ingredient.

* * * * *